(12) United States Patent
Jolly et al.

(10) Patent No.: US 8,428,688 B2
(45) Date of Patent: Apr. 23, 2013

(54) AUTOMATIC FEMUR SEGMENTATION AND CONDYLE LINE DETECTION IN 3D MR SCANS FOR ALIGNMENT OF HIGH RESOLUTION MR

(75) Inventors: Marie-Pierre Jolly, Hillsborough, NJ (US); Christopher V. Alvino, Plainsboro, NJ (US); Benjamin L. Odry, West New York, NJ (US); Jens Gühring, Monmouth Junction, NJ (US)

(73) Assignee: Siemens Aktiengesellschaft, München (DE)

( * ) Notice: Subject to any disclaimer, the term of this patent is extended or adjusted under 35 U.S.C. 154(b) by 569 days.

(21) Appl. No.: 12/426,323

(22) Filed: Apr. 20, 2009

(65) Prior Publication Data

US 2010/0121175 A1    May 13, 2010

Related U.S. Application Data

(60) Provisional application No. 61/112,876, filed on Nov. 10, 2008.

(51) Int. Cl.
*A61B 5/00*    (2006.01)
(52) U.S. Cl.
USPC ........... 600/410; 600/417; 600/425; 382/128; 382/130; 382/132; 382/173; 345/419; 345/423
(58) Field of Classification Search .................. 345/419, 345/423; 382/128, 130, 131, 173; 600/407, 600/410; 606/102; 623/41.12, 20.29
See application file for complete search history.

(56) References Cited

U.S. PATENT DOCUMENTS

| | | | | |
|---|---|---|---|---|
| 5,682,886 A | * | 11/1997 | Delp et al. | 600/407 |
| 6,961,454 B2 | * | 11/2005 | Jolly | 382/131 |
| 6,973,212 B2 | * | 12/2005 | Boykov et al. | 382/173 |
| 7,167,172 B2 | * | 1/2007 | Kaus et al. | 345/419 |
| 7,346,203 B2 | * | 3/2008 | Turek et al. | 382/131 |
| 7,400,757 B2 | * | 7/2008 | Jolly et al. | 382/131 |
| 7,799,077 B2 | * | 9/2010 | Lang et al. | 623/14.12 |
| 2002/0048401 A1 | * | 4/2002 | Boykov et al. | 382/173 |
| 2003/0020714 A1 | * | 1/2003 | Kaus et al. | 345/423 |
| 2003/0035573 A1 | * | 2/2003 | Duta et al. | 382/128 |
| 2003/0069494 A1 | * | 4/2003 | Jolly | 600/410 |

(Continued)

OTHER PUBLICATIONS

Jose L. Marroquin, Edgar Arce Santana, and Salvador Botello, Hidden Markov Measure Field Models for Image Segmentation, IEEE Transactions on Pattern Analysis and Machine Intelligence, vol. 25, No. 11, Nov. 2003.*

*Primary Examiner* — Unsu Jung
*Assistant Examiner* — Serkan Akar
(74) *Attorney, Agent, or Firm* — Donald B. Paschburg

(57) ABSTRACT

A method for automatic femur segmentation and condyle line detection. The method includes: scanning a knee of a patient with medical imaging equipment to obtain 3D imaging data with such equipment; processing the obtained 3D imaging data in a digital processor to determine two lines tangent to the bottom of the knee condyles in an axial and a coronal plane; and automatically scanning the patient in the defined plane. The processing includes: determining an approximate location of the knee; using the determined the location to define a volume of interest; segmenting the femur in the defined volume of interest; and determining a bottom point on the femur portion on a right side and a left side of the segmented femur in an axial and a coronal slice to determine the two lines.

9 Claims, 6 Drawing Sheets

U.S. PATENT DOCUMENTS

| | | | |
|---|---|---|---|
| 2004/0015072 A1* | 1/2004 | Pelletier et al. | 600/410 |
| 2004/0204760 A1* | 10/2004 | Fitz et al. | 623/14.12 |
| 2005/0084145 A1* | 4/2005 | Pelletier et al. | 382/130 |
| 2005/0085709 A1* | 4/2005 | Pelletier et al. | 600/410 |
| 2005/0113663 A1* | 5/2005 | Tamez-Pena et al. | 600/407 |
| 2005/0238215 A1* | 10/2005 | Jolly et al. | 382/128 |
| 2006/0285734 A1* | 12/2006 | Haider et al. | 382/128 |
| 2007/0025616 A1* | 2/2007 | Grady et al. | 382/173 |
| 2007/0100462 A1* | 5/2007 | Lang et al. | 623/20.29 |
| 2007/0185498 A2* | 8/2007 | Lavallee | 606/102 |
| 2007/0260135 A1* | 11/2007 | Rousson et al. | 600/407 |
| 2008/0004517 A1* | 1/2008 | Bhandarkar et al. | 600/407 |
| 2008/0075348 A1* | 3/2008 | Rappaport et al. | 382/132 |

* cited by examiner

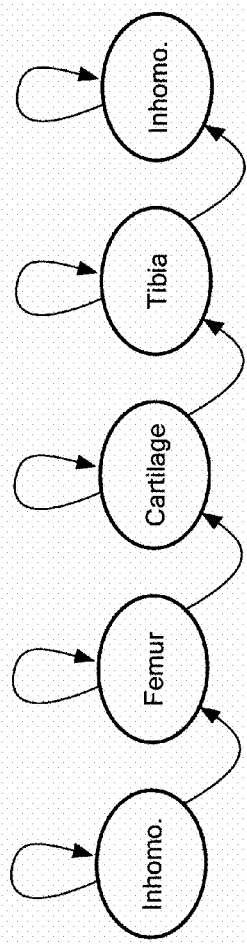
FIG. 3
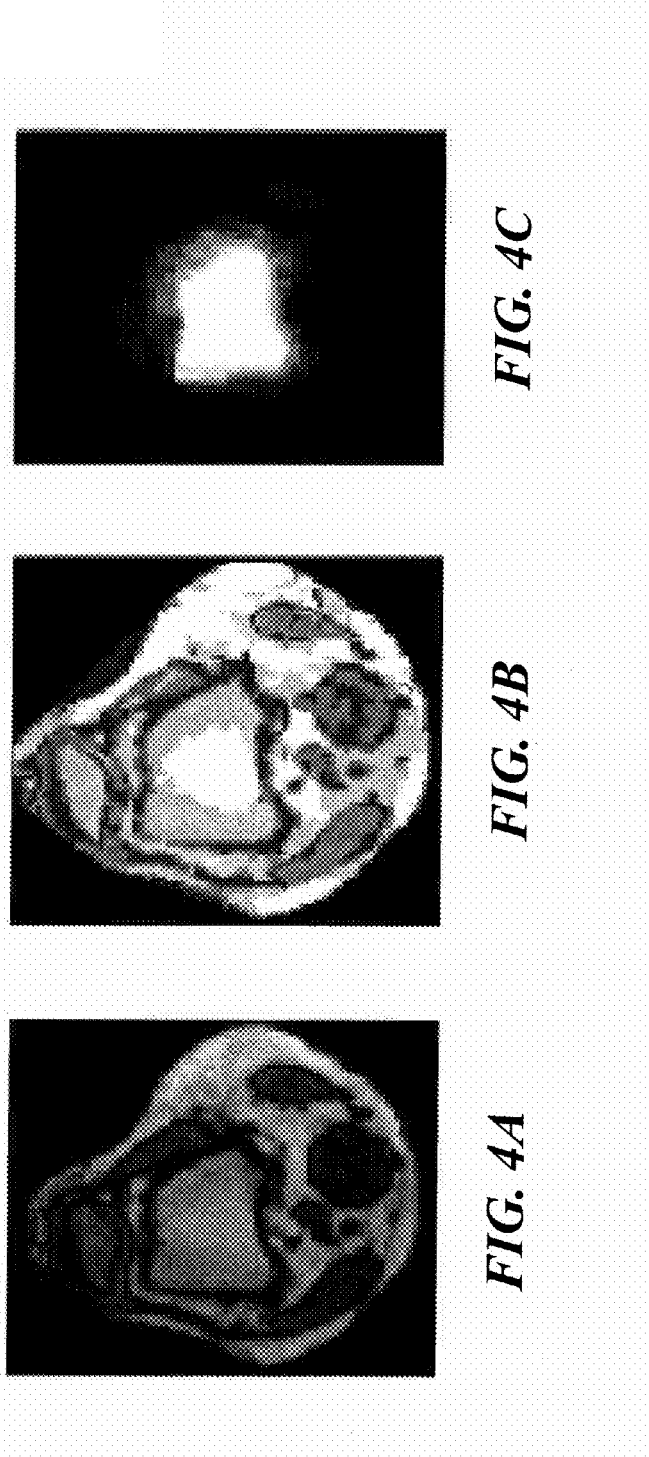
FIG. 4A  FIG. 4B  FIG. 4C

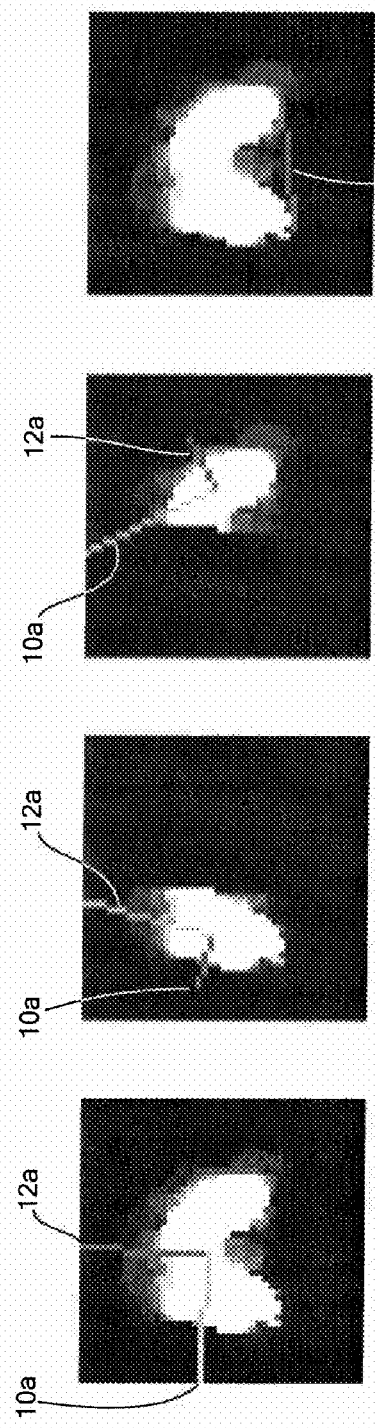
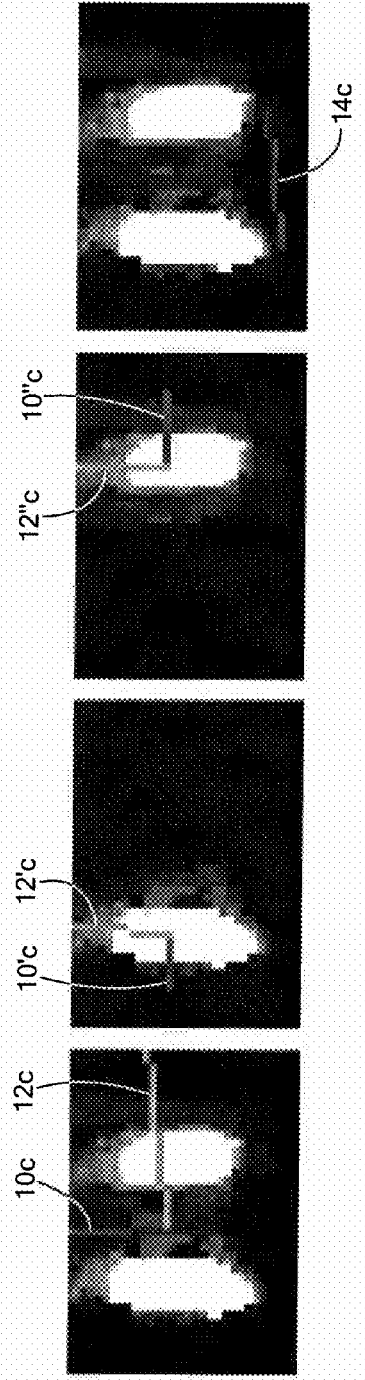
FIG. 5A  FIG. 5B  FIG. 5C  FIG. 5D
FIG. 6A  FIG. 6B  FIG. 6C  FIG. 6D

AUTOMATIC FEMUR SEGMENTATION AND CONDYLE LINE DETECTION IN 3D MR SCANS FOR ALIGNMENT OF HIGH RESOLUTION MR

CROSS-REFERENCE TO RELATED APPLICATIONS

This application claims priority from U.S. Provisional application No. 61/112,876 filed Nov. 10, 2008, the entire subject matter thereof being incorporated herein by reference.

TECHNICAL FIELD

This invention relates generally to methods for automatic femur segmentation and condyle line detection in three-dimensional (3D) magnetic resonance (MR) scans and more particularly to methods for automatic femur segmentation and condyle line detection in 3D MR scans for alignment of High resolution MR.

BACKGROUND

As is known in the art, the meniscus is a pad of cartilaginous tissue that separates the femur from the tibia. It serves to disperse friction between these two bones. The cruciate ligaments (anterior: ACL and posterior: PCL) connect the femur to the tibia and are the most critical ligaments to image within the knee, as they are commonly torn during sports related dislocation, torsion, or hyper-extension of the knee.

When imaging the meniscus and cruciate ligaments with MR scans, the usual plane selected is a transverse (axial) view. However, a more appropriate plane for imaging these anatomies is that which is adjacent to and also connects the lateral and medial condyles of the femur. A clinical technician could manually define this plane by following a specific procedure to identify the following landmarks as shown in FIG. 1: a) the center of the pit between the medial and lateral condyles (fossa intercondylaris); b) the posterior margins of the medial and lateral condyles of the femur in the same axial slice (axial intercondyle line); c) the lower margins of the medial and lateral condyles of the femur in the coronal view (coronal intercondyle line). The realignment of the localizer along the plane defined by these new directions yields an acquisition in the knee frame of reference which is much more appropriate for diagnosis. It is desirable to have automated and reproducible precision planning by automatically determining this plane for precise scans. One technique for automated scan planning for knee joints was described in a paper presented by D. Bystrov, V. Pekar, S. Young, S. P. M. Dries, H. S. Heese, and A. M. van Muiswinkel, "Automated planning of MRI scans of knee joints," in *SPIE Conference Series*. March 2007, vol. 6509 and its clinical accuracy was evaluated in F. E. Lecouvet, J. Claus, P. Schmitz, V. Denolin, C. Bos, and B. C. Vande Berg, "Clinical evaluation of automated scan prescription of knee MR images," *Journal of Mag. Res. Imag.*, vol. 29, pp. 141-145, 2009. The method of D. Bystrov et al above, uses an optimization scheme that uses an active shape model to guide a deformable model, which is in turn attracted to locally detected surfaces. The method handles bending of the knee with an explicit bending parameter that is also estimated.

SUMMARY

A method is provided for automatic femur segmentation and condyle line detection. The method includes: scanning a knee of a patient with medical imaging equipment to obtain 3D imaging data with such equipment; processing the obtained 3D imaging data in a digital processor to determine two lines tangent to the bottom of the knee condyles in an axial and a coronal plane; and automatically scanning the patient in response in a plane having the determined lines. The processing includes: determining an approximate location of the knee; using the determined location to define a volume of interest; segmenting the femur above the located knee in the defined volume of interest; and determining a bottom point on the femur on a right side and a left side of the segmented femur to determine the two lines.

The method for determining this scan plane automatically from the data is multiphase. The method uses medical imaging equipment generated data, typically from MR imaging equipment, to first determine the approximate location of the knee joint using a very fast and robust, yet slightly inaccurate algorithm based on Hidden Markov Models (HMMs). The method then uses this location to define a volume of interest and then segment the femur in the defined volume of interest using, for example, the random walker algorithm. Condyle lines in the axial and coronal images of the segmented condyle are defined by finding the bottom point of the femur on the left and right side of the segmented femur.

In accordance with the present invention, a method is provided for automatic femur segmentation and condyle line detection. The method includes: scanning a knee of a patient with medical imaging equipment to obtain 3D imaging data with such equipment; processing the obtained 3D imaging data in a digital processor to determine two lines tangent to the bottom of knee condyles in an axial and a coronal plane; and automatically scanning the patient in a plane having both determined lines.

In one embodiment, the processing comprises: determining an approximate location of the knee; segmenting the femur above the knee in the determined approximate location; and determining a bottom point on the femur on a right side and a left side of the segmented femur to determine the two lines.

In one embodiment, the determining an approximate location of the knee comprises determining leg boundaries in two axial planes comprising determining regions which are air and regions which are leg in the two axial planes, one being an upper plane within the femur, and one being a lower plane within the tibia and determining the center of the leg in each of the two selected axial planes using the determined leg boundaries.

In one embodiment, the method uses 3D imaging data obtained from 3D imaging equipment having an initial scan orientation of a leg to generate an image of the leg and determine from the image an approximate location of a knee joint of the leg using, for example, a very fast algorithm based on Hidden Markov Models. The method then uses the determined location to define a volume of interest in the image and segment the femur in the image using the random walker algorithm. The method then extracts condyle lines of the segmented femur in axial and coronal images by determining bottom points of the segmented femur. Next, the method determines a transformation matrix to define a new scan orientation from the extracted condyle lines.

In one embodiment, the method extracts the knee frame of reference from 3D MR isotropic scans. The method determines two lines that are tangent to the bottom of the condyles in an axial and a coronal plane to extract the knee frame of reference. The method includes: initial detection of the knee joint using Hidden Markov Models; femur segmentation using Random Walker segmentation; and condyle detection.

With such method a model of the knee is not used. Also, the use of local surface coils, which is typical in clinical practice, and which prevents large angulations of the knee is not required.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A Fossa intercondylaris; FIG. 1C Coronal intercondyle line;

FIG. 2A shows an intensity feature that acts as sequence of Hidden Markov Model (HMM) observations and FIG. 2B shows the most likely state sequence;

FIG. 3. Each region of interest in the knee is modeled by a state in the HMM. The arrows above each state correspond to self-transitions and the arrows between states correspond to state changes;

FIG. 4. Femur segmentation: (a) Original axial slice; (b) Range based multilabel fuzzy connectedness segmentation; (c) Random walker femur probabilities;

FIG. 5A shows a femur probability map and main axes (10a and 12a); FIG. 5B shows left component and its main axes (10'a and 12'a); FIG. 5C shows right component and its main axes (10"a and 12"a); and, FIG. 5D shows the detected intercondyle line 14a tangent to the bottom of the knee condyles in an axial image;

FIG. 6A shows a femur probability map and main axes (10c and 12c); FIG. 6B shows left component and its main axes (10'c and 12'c); FIG. 6C shows right component and its main axes (10"c and 12"c); and, FIG. 6D shows the detected intercondyle line 14c;

Like reference symbols in the various drawings indicate like elements.

DETAILED DESCRIPTION

Figure 8:
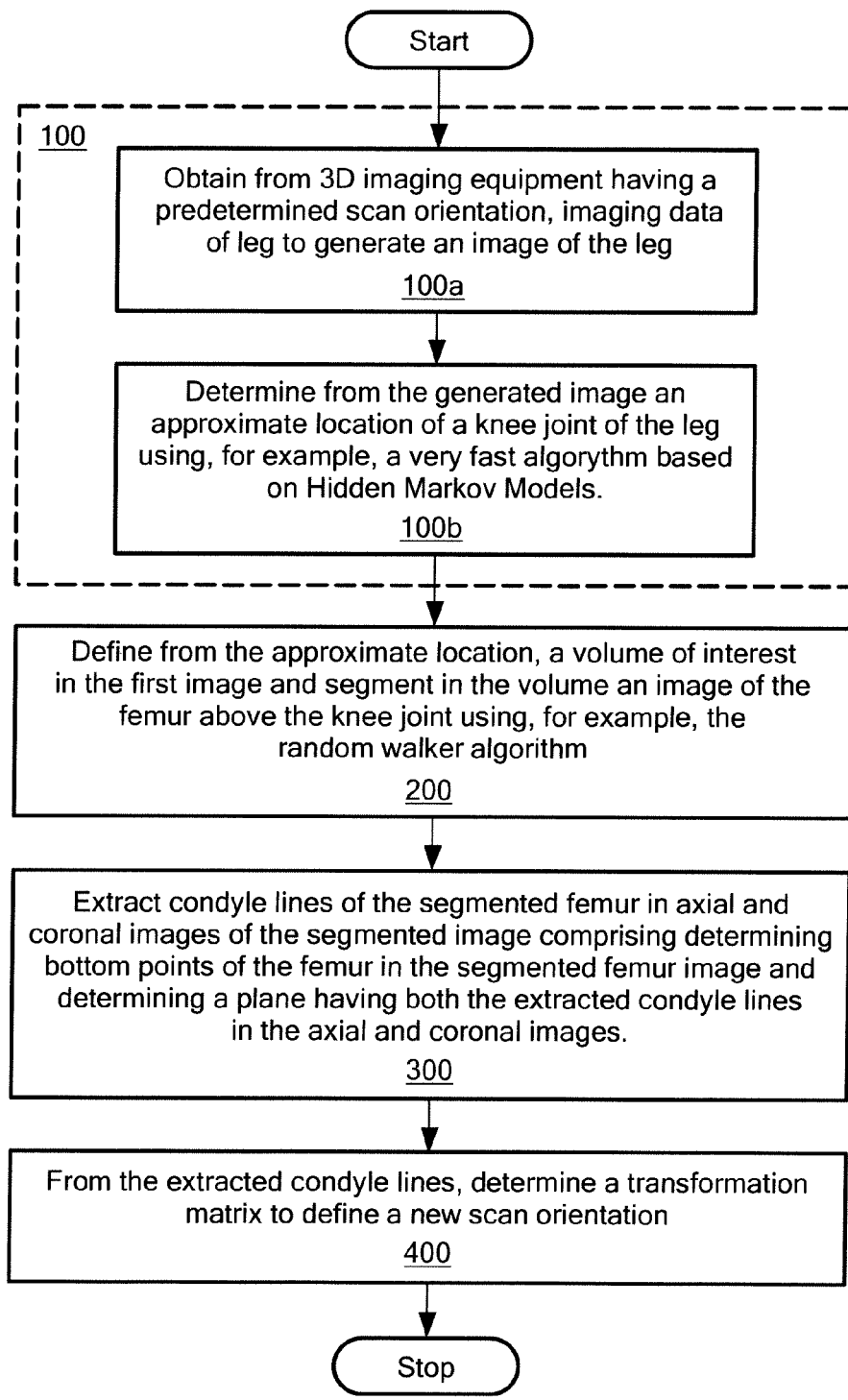
FIG. 8 is a flowchart of a method for automatic femur segmentation and condyle line detection in three-dimensional (3D) magnetic resonance (MR) scans according to the invention.

Referring now to FIG. 8, a flowchart of a method for automatic femur segmentation and condyle line detection in three-dimensional (3D) magnetic resonance (MR) scans is shown. Briefly, the method automatically scans a knee of a patient with MR equipment, not shown to obtain 3D imaging data and then, a digital processor, not shown, uses the obtained data, to determine two lines that are tangent to the bottom of the knee condyles in an axial and a coronal plane. Referring to FIG. 8, the method comprises three major parts, initial detection of the knee joint (Step 100), femur segmentation (Step 200), and finally condyle detection (Step 300).

Thus, in Step 100, the method obtains from 3D imaging equipment having a predetermined scan orientation, imaging data of leg to generate an image of the leg (Step 100a). Next, the method determine from the generated image an approximate location of a knee joint of the leg using, for example, a very fast algorithm based on Hidden Markov Models (Step 100b).

After initial detection of the knee, the method segments the femur here by, as shown in FIG. 8), defining from the approximate location, a volume of interest in the image and segmenting in the volume an image of the femur using, for example, the random walker algorithm (Step 200).

Next, the condyle is detected here, as shown in FIG. 8, by extracting condyle lines of the segmented femur in axial and coronal images of the segmented image comprising determining bottom points of the femur in the segmented femur image on the left and right side of bone in the segmented image and determining a plane having both the extracted condyle lines in the axial and coronal images (Step 300). The extracted lines (shown in FIG. 7) define a plane. The MR equipment, in response to the defined plane, automatically scans the patient in the defined plane at high resolution in the knee frame of reference that is ideal for physicians to look at the knee and diagnose problems.

The method determines from the extracted condyle lines a transformation matrix to define a new scan orientation (400) and a new scan is performed. The knee is then imaged in its frame of reference.

More particularly:

1. Knee Joint Detection (Step 100)

This knee joint detection consists of three phases: Leg boundary determination, in which the boundary of the leg is determined in several axial images; Feature extraction, in which features that contain statistics about the intensity profiles along the centerline of the knee are detected; and Hidden Markov Model (HMM) state estimation, in which the optimal state sequence that could have produced the observed intensity features is determined.

More particularly, only a small portion of the knee region is present in the scan. That is, the scan should not include anatomy above the femur such as the pelvis, and the scan should not include anatomy below the tibia such as the foot. The portion of the leg that is in the scan range should be sufficiently straight. This can be relaxed by moving to a slightly more general version of the algorithm with little additional computational expense. Only one knee (and not two knees) should be present in the scan region. This is easy to satisfy with simple preprocessing steps.

With these criteria in place, this portion of the algorithm proceeds as follows

Algorithm Steps

1. Leg Boundary Determination: In two axial planes, one being an upper plane within the femur, and one being a lower plane within the tibia, the method determines which regions are air and which regions are leg.

1.1. This can typically be obtained by implementing a simple threshold to obtain a binary mask. In practice this mask is refined by performing a morphological opening operation (erosion followed by dilation).

1.2. The boundaries of these masks are determined within each 2D axial plane separately. These boundaries are used to determine the center point of the leg in each of the two selected axial slices.

2. Feature Extraction:

2.1. Line connection: A three-dimensional straight line that connects these two center points from Algorithm Step 1.2 is then placed in the 3D volume.

2.2. Intensity Sampling: Intensities are then sampled based on the geometry of this line at fixed, equally-spaced intervals. The spacing between points can nominally be set to some spacing (such as 0.7 mm).

2.3. Feature Generation: From these intensities, features can be generated that discriminate between bone intensity versus cartilage intensity. One specific feature that was successful was, for each point on the line, sampling a set of intensities within a circular disc orthogonal to the line, and determining the $75^{th}$ percentile intensity.

2.4. Feature Normalization: From these generated features, the method then normalizes the intensities in the features by subtracting the mean intensity within a sliding window. This mean subtracted feature is then transformed by: $\hat{f}(x)=\alpha f(x)+\beta$, where $f(x)$ is the mean subtracted feature and $\hat{f}(x)$ is the normalized mean subtracted feature. The values of $\alpha$ and $\beta$ are chosen so that the $90^{th}$ percentile intensity of the mean subtracted feature is mapped to the value of 1 and the $10^{th}$ percentile intensity of the mean subtracted feature is mapped to the value of −1. The values that are used as observations for the Hidden Markov Model (HMM) are $\hat{f}(x)$.

3. Hidden Markov Model (HMM) State Estimation:

3.1. From Observations to State Estimates: The features generated from section 2.3 are then considered state output observations for a Hidden Markov Model for which each state's output is described by a Gaussian Mixture Model (GMM) probability distribution. Here, the Viterbi algorithm is used to determine the most likely state sequence that could have caused this observation sequence. See more details on the Hidden Markov Model section below.

3.2. From State Estimates to Cartilage Positions: The positions on the line that corresponded to the cartilage state in the Hidden Markov Model (HMM) are then labeled. The middle of the cartilage region is then considered to be the most likely cartilage center.

4. Final Output:

4.1. The plane orthogonal to the line found in Algorithm Step 2.1 and which crosses through the cartilage center point found in Algorithm Step 3.2 is considered be to an approximate plane of interest.

4.2. The logarithm of the probability of the most likely state sequence obtained by Algorithm Step 3.2 gives some indication of the level of reliability of this algorithm's performance.

It is to be noted that in section 2 of the algorithm description, the line connecting the center points (from Algorithm Step 1.2), which is intended to run through the knee, need not be straight. Alternatively, it is possible to compute the leg boundary (as in Algorithm Step 1) at several axial slices and then compute a curved line that traverses through that knee. This would effectively relax Algorithm Requirement 2.

Hidden Markov Model Details

The Hidden Markov Model (HMM) introduced in Algorithm Step 3, will now be described in further detail.

In two axial planes, one being an upper plane within the femur, and one being a lower plane within the tibia, the method determines which regions are air and which regions are leg. The method then determines the center point of the leg in each of two axial slices, a three dimensional straight line that connects these two center points is then placed in the three dimensional volume. The obtained Magnetic Resonance (MR) voxel intensities are then sampled along this centerline at fixed intervals. For each point on the centerline, the method samples a set of the voxel intensities within a circular disc of intensities orthogonal to the centerline, and then determines the $75^{th}$ percentile intensity. These intensities are normalized by subtracting the mean intensity within a sliding window of intensities. This normalized (i.e., mean subtracted feature) is then transformed by: $\hat{f}(x)=\alpha f(x)+\beta$, where $f(x)$ is the mean subtracted feature and $\hat{f}(x)$ is the normalized mean subtracted feature. The values of $\alpha$ and $\beta$ are selected so that the 10th percentile intensity and the 90th percentile intensity of the mean subtracted feature are mapped to −1 and 1, respectively. The values, $\hat{f}(x)$ are then used as observations for the HMM (e.g., FIG. 2A)

These features are then considered state output observations for an HMM for which each state's output is described by a Gaussian Mixture Model (GMM) probability distribution. The Viterbi algorithm is used to determine the most likely state sequence that could have caused this feature observation sequence.

For an introduction to HMM's, see L. R. Rabiner, "A tutorial on hidden Markov models and selected applications in speech recognition," *Proceedings of the IEEE*, vol. 77, no. 2, pp. 257-286, 1989. The HMM that is used to model the spatially varying feature distribution contains five states and is shown in FIG. 3. In FIG. 3, each region of interest in the knee is modeled by a state in the HMM. The arrows above each state correspond to self-transitions and the arrows between states correspond to state changes. Here, the method selects five states to model the transition from femur to cartilage and the transition from cartilage to tibia while also modeling the dips in intensities that often occur in MR scans at the top and bottoms of the scans. Associated with each state is a separate GMM that describes its observation distributions. The method selects the individual GMM's empirically to correspond to common feature value ranges for each of the states, but it is also possible to train them in a supervised learning fashion. More particularly, an intensity model for the different components in the HMM: bone, cartilage, . . . is created empirically, or alternatively, a training process can be used by providing a number of examples of cartilage and bones and then teaching a learning system, neural network or other process what the intensity model should be. Also, the method selects probabilities for the transition events that correspond to typical spatial lengths for different states (see L. R. Rabiner, above). The algorithm is robust to reasonable choices of these parameters.

Finally, the method sets the initial state probabilities to be 50% in the first inhomogeneity region and 50% in the femur region. The method also enforces that the final state lies in either the tibia state or the final inhomogeneity state, thus guaranteeing passage through the desired cartilage state.

Figures 1A, 1B, 1C:
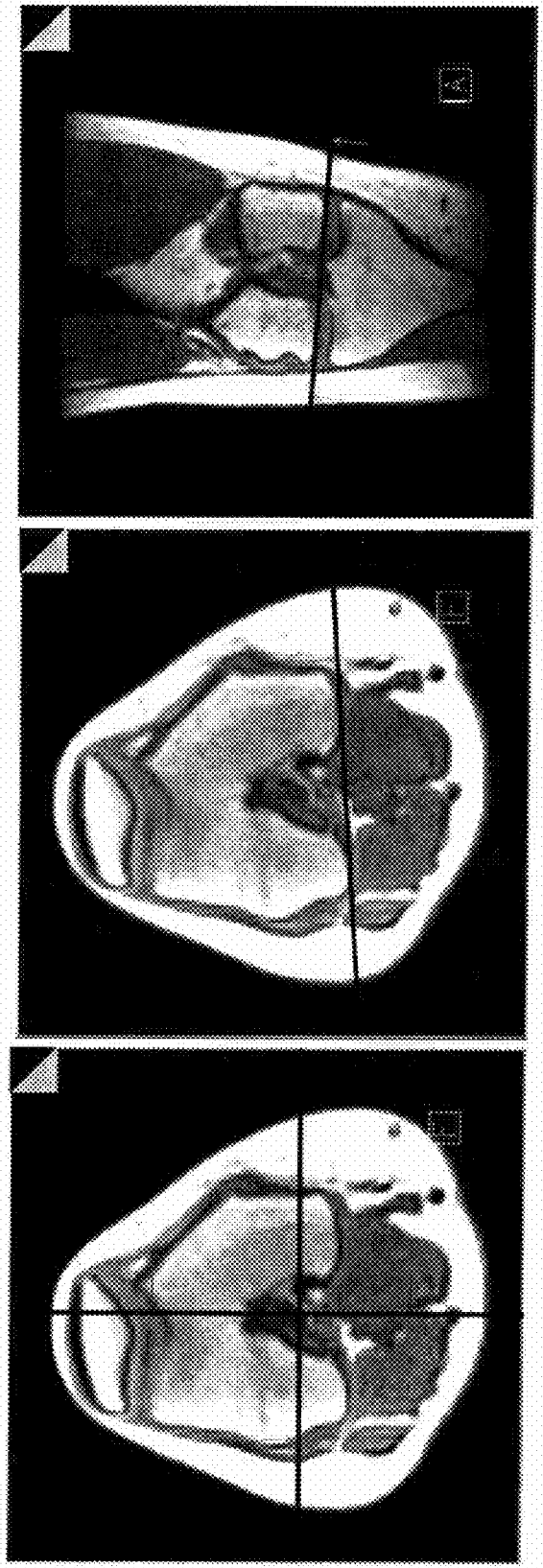
FIGS. 1A-1C illustrate steps in identifying the landmarks to define the knee frame of reference.
Figure 2A:
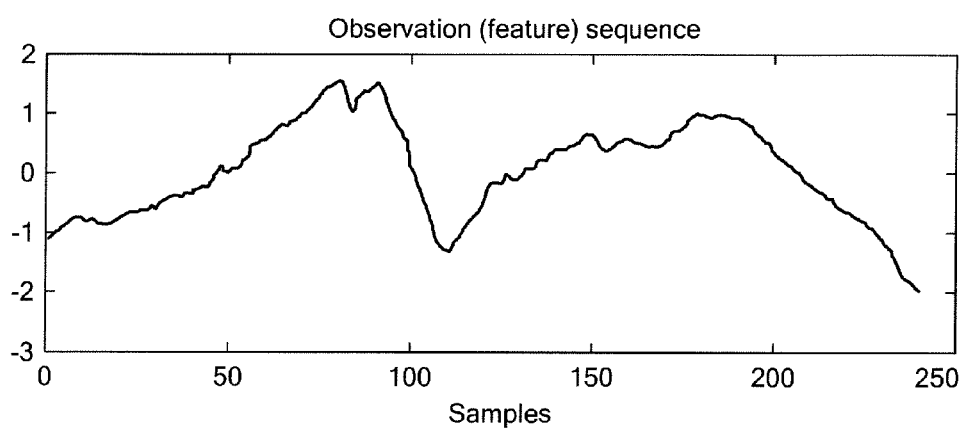
Figure 2B:
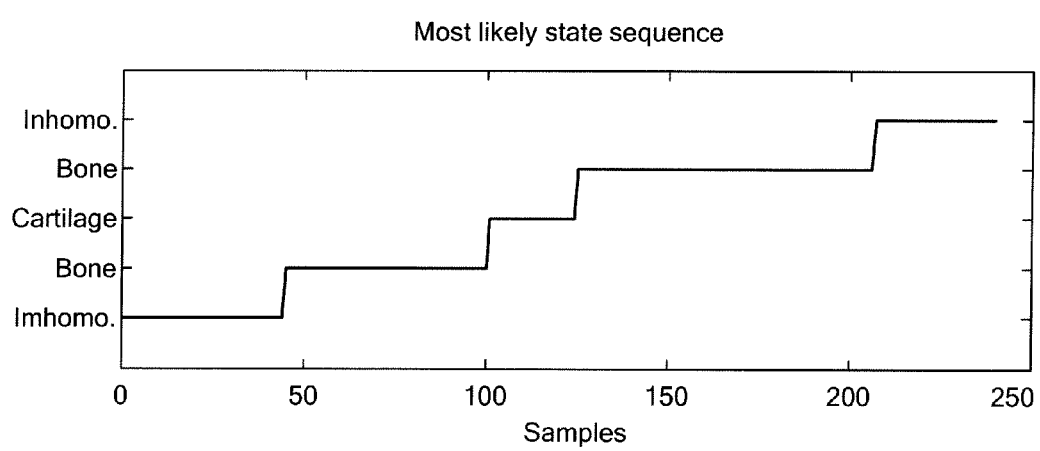
FIG. 2B Axial intercondyle line.

FIG. 2B shows an example of the state sequence determined by the Viterbi algorithm. More particularly, FIG. 2A shows intensity features that act as sequence of Hidden Markov Model (HMM) observations and FIG. 2B shows the most likely state sequence. The positions on the centerline that corresponded to the cartilage state (or the knee joint) were correctly labeled by the HMM. The middle of the cartilage region was considered to be the most likely cartilage center.

2. Femur Segmentation (Step 200)

Once the approximate location of the knee joint has been determined, the algorithm used by the method identifies the femur in order to precisely locate the condyle line in both axial and coronal views. The location of the knee joint defines a point in the 3D volume which in turn defines a small volume of interest (VOI) consisting of a number of slices around this point, with more slices upwards, toward the femur. This small VOI is then processed by the next step of the algorithm. In the first step, the pixels inside the leg are simply adaptively thresholded from the almost black background using Otsu's algorithm (see N. Otsu, "A threshold selection method from gray level histograms," *IEEE Trans. Systems, Man and*

Cybernetics, vol. 9, pp. 62-66, 1979). Then, the histogram of the leg pixels is divided into four main regions (roughly corresponding to muscle, bone, fat and skin) using three iterations of Otsu's algorithm. The centers of these four regions are used as the seeds of the range based multiseeded fuzzy connectedness algorithm proposed in M.-P. Jolly and L. Grady, "3D general lesion segmentation in CT," in *Int. Symp. Biomedial Imaging*, 2008, pp. 796-799 which is a modification of the multiseeded fuzzy connectedness algorithms proposed in J. K. Udupa and S. Samarasekera, "Fuzzy connectedness and object definition: Theory, algorithms, and applications in image segmentation," *GMIP*, vol. 58, no. 3, pp. 246-261, 1996. G. T. Herman and B. M. Carvalho, "Multiseeded segmentation using fuzzy connectedness," *IEEE Trans. Pattern Analysis and Machine Intelligence*, vol. 23, no. 5, pp. 460-474, 2001. The idea is to use the range of gray levels along the path in the cost function so that similar pixels are grouped together.

The largest, most compact, closest to the center, connected component is extracted in the top slice. It is expected to belong to the femur and will be used to seed the random walker algorithm (see L. Grady, "Random walks for image segmentation," *IEEE Trans. Pattern Analysis and Machine Intelligence*, vol. 28, no. 11, pp. 1768-1783, 2006) as follows. In the top slice, pixels that are a certain distance inside the chosen connected component are seeded as foreground, whereas pixels which are on the edges of the leg are seeded as background. Pixels on the bottom slice are also seeded as background. Given foreground and background seeds, the random walker algorithm determines the probability that a random walker released from that voxel and allowed to walk randomly to neighboring voxels (in 3D) reaches a foreground seed. The image data biases the walker to avoid crossing large intensity gradients when considering which neighboring voxel to "walk" to. As was shown in Grady, above, it is possible to compute these probabilities analytically, without simulating random walks. The random walker algorithm produces segmentations that are very robust to weak boundaries and noise. This femur probability segmentation is the basis for the condyle detection algorithm. FIGS. 4A-4C shows results for the different steps of the femur segmentation algorithm in an axial slice. More particularly, FIG. 4A shows an original axial slice of a femur; FIG. 4B shows range based multilabel fuzzy connectedness femur segmentation; and FIG. 4C shows random walker femur probabilities, note that the bright central region shows the maximum probability for a femur.

3. Condyle Detection (Step 300)

The goal is then to find the axial slice where the pit between the condyles is most prominent and determine the intercondyle line in that slice. Referring to FIGS. 5A-5D, in each axial slice, the femur is divided into the left and right side of its center of mass. More particularly, FIG. 5A-5D shows condyle detection in axial slices: FIG. 5A shows a femur probability map and main axes ($10a$ and $12a$); FIG. 5B shows left component and its main axes ($10'a$ and $12'a$); FIG. 5C shows right component and its main axes ($10''a$ and $12''a$); and, FIG. 5D shows the detected intercondyle line $14a$ tangent to the bottom of the knee condyles in an axial slice. Principal component analysis is applied to each side and the object is rotated so that its longest axis aligns with the x-axis. The maximum and average femur probabilities are computed along the y-axis for each x-coordinate. The condyle margin is then located at the first x-coordinate where either the maximum or the average probability exceeds a threshold.

Then, for each slice i, the method calculates $S_i^L$, the average of the probabilities between the left side center and the left condyle, and $S_i^R$, the average of the probabilities between the right side center and the right condyle. The method also calculates $S_i^T$, the average probability between the center of the femur and the middle point in the intercondyle line. The method then computes $S_i = S_i^L + S_i^R - S_i^T$ and finds $S_{max} = \max_i (S_i)$. To find the best axial slice and determine the posterior margins of the medial and lateral condyles, the method examines all axial slices whose $S_i$ is within 75% of $S_{max}$ and the method selects the one with most posterior condyle positions.

This axial intercondyle line is used to generate an MPR of the femur probabilities in the coronal direction and the same process is applied to extract the intercondyle line in that slice. FIGS. 6A-6D shows condyle detection in the coronal slice: FIG. 6A shows a femur probability map and main axes ($10c$ and $12c$); FIG. 6B shows left component and its main axes ($10'c$ and $12'c$); FIG. 6C shows right component and its main axes ($10''c$ and $12''c$); and, FIG. 6D shows the detected intercondyle line $14c$.

Figure 7A:
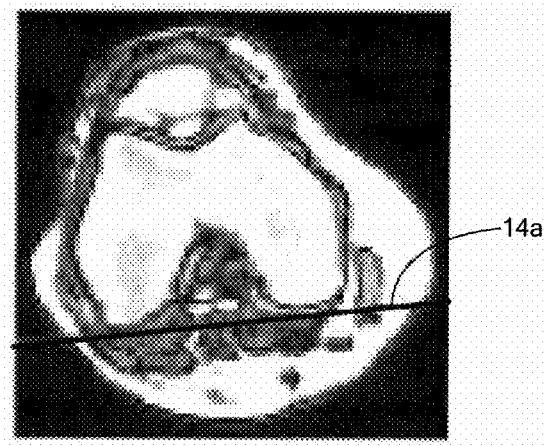
FIG. 7A shows in the intercondyle line 14a in an axial slice and FIG. 7B shows the intercondyle line 14c in the coronal multiplanar reformatted view (MPR)
Figure 7B:
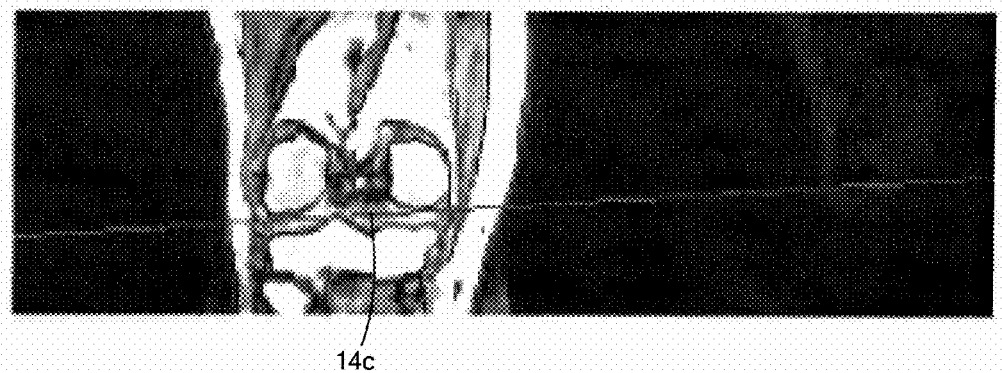

Finally, FIG. 7A shows in the intercondyle line $14a$ in an axial slice and FIG. 7B shows the intercondyle line $14c$ in the coronal MPR. The intercondyle lines $14a$, $14c$ shown in FIGS. 7A and 7B define a plane than can be used to scan the knee at high resolution in its frame of reference, for best diagnosis by the physicians.

A number of embodiments of the invention have been described. Nevertheless, it will be understood that various modifications may be made without departing from the spirit and scope of the invention. Accordingly, other embodiments are within the scope of the following claims.

What is claimed is:

1. A method for femur segmentation and condyle line detection, comprising:
   scanning a knee of a patient with medical imaging equipment to obtain 3D imaging data with such equipment;
   processing the obtained 3D imaging data in a digital processor to determine two lines tangent to the bottom of knee condyles in an axial and a coronal plane; and
   automatically scanning the patient in a plane defined by the determined lines,
   wherein one of the lines is included in an axial slice of the 3D imaging data, the axial slice being determined by calculating, for each axial slice in the 3D imaging data, a first average of probabilities between a left side center of a segmented femur and a left condyle, a second average of probabilities between a right side center of the segmented femur and a right condyle, and a third average probability between the center of the segmented femur and a middle point in an inter-condyle line, obtaining a value of the axial slice by summing the first and second average probabilities and subtracting the third probability from this sum, identifying the axial slices whose values are within a predetermined range, and selecting, from the identified axial slices, the axial slice with the most posterior condyle positions.

2. The method recited in claim 1 wherein the processing comprises:
   determining an approximate location of knee;
   segmenting the femur of the knee in the determined approximate location;
   determining a bottom point on the femur portion on the right side and the left side of the segmented femur in the axial slice and a coronal view to determine the two lines.

3. The method recited in claim 2 wherein the determining an approximate location of the knee comprises determining leg boundaries in two axial planes comprising determining regions which are air and regions which are leg in the two axial planes, one being an upper plane within the femur, and one being a lower plane within the tibia and determining the center of the leg in each of the two selected axial planes using the determined leg boundaries.

4. The method recited in claim 1 wherein the probabilities between a left side center of a segmented femur and a left condyle and the probabilities between a right side center of the segmented femur and a right condyle include random walker probabilities.

5. A method for femur segmentation and condyle line detection, comprising:
scanning a knee of a patient with medical imaging equipment to obtain 3D imaging data with such equipment;
processing the obtained 3D imaging data in a digital processor to determine two lines tangent to the bottom of knee condyles in an axial plane and in a coronal plane; and
scanning the patient in a plane defined by the determined lines,
wherein one of the lines is included in an axial slice of the 3D imaging data, the axial slice being determined by calculating, for each axial slice in the 3D imaging data, a first average of probabilities between a left side center of a segmented femur and a left condyle, a second average of probabilities between a right side center of the segmented femur and a right condyle, and a third average probability between the center of the segmented femur and a middle point in an inter-condyle line, obtaining a value of the axial slice by summing the first and second average probabilities and subtracting the third probability from this sum, identifying the axial slices whose values are within a predetermined range, and selecting, from the identified axial slices, the axial slice with the most posterior condyle positions.

6. The method recited in claim 5 wherein the method uses the obtained 3D imaging data having an initial scan orientation of a leg to generate an image of the leg and determines from the image an approximate location of a knee of the leg and then using the determined location defines a volume of interest segments the femur above the knee.

7. The method recited in claim 6 wherein the method extracts condyle lines of the segmented femur in the axial slice and a coronal image by determining bottom points of the segmented femur.

8. The method recited in claim 7 further including determining a transformation matrix to define a new scan orientation from the extracted condyle lines.

9. The method recited in claim 5 wherein the method uses Hidden Markov Models to approximate the location of a knee.

* * * * *